United States Patent [19]

Sakata et al.

[11] Patent Number: 5,030,610

[45] Date of Patent: Jul. 9, 1991

[54] ACIDIC GAS ABSORBENT AND PROCESS FOR PRODUCTION THEREOF

[75] Inventors: Yoshitsugu Sakata, Otsu; Shinogu Fukahori, Nishinomiya; Hiroyuki Kodera, Amagasaki; Kenzi Iwata, Higashiosaka, all of Japan

[73] Assignee: Wako Pure Chemical Industries, Ltd., Osaka, Japan

[21] Appl. No.: 509,523

[22] Filed: Apr. 16, 1990

[30] Foreign Application Priority Data

Apr. 17, 1989 [JP] Japan .................... 01-096909

[51] Int. Cl.⁵ ............... B01J 20/04; C09K 3/00; C01B 31/20; C01B 7/00
[52] U.S. Cl. ................... 502/400; 55/68; 55/71; 252/189; 423/230; 423/240
[58] Field of Search ............ 502/400; 423/230; 252/189

[56] References Cited

U.S. PATENT DOCUMENTS 2,322,206  6/1943  Gardenier ............. 252/189
3,557,011  1/1971  Colombo et al. ....... 423/230
4,552,767  11/1985 Saleer et al. .......... 502/400

Primary Examiner—Paul E. Konopka
Attorney, Agent, or Firm—Armstrong, Nikaido, Marmelstein, Kubovcik & Murray

[57] ABSTRACT

A molded acidic gas absorbent produced by press molding powders, etc. of calcium hydroxide and one or more powders, etc. of alkali metal hydroxides and alkaline earth metal hydroxides except for calcium hydroxide, impregnating the molded article with water, followed by heat treatment while maintaining a predetermined amount of water therein is effective for absorbing an acidic gas such as $CO_2$ in air and a narcotic gas.

7 Claims, 1 Drawing Sheet

ACIDIC GAS ABSORBENT AND PROCESS FOR PRODUCTION THEREOF

BACKGROUND OF THE INVENTION

This invention relates to an absorbent for acidic gases, such as carbon dioxide, HCl gas, HF gas, etc., used to clean air, narcotic gas, etc., and a process for the production thereof.

Soda lime is widely used as an absorbent for carbon dioxide contained in air and narcotic gas. In general, it is produced by immersing calcium oxide in a concentrated sodium hydroxide aqueous solution, subjecting the solution to heat treatment and pulverizing the resultant aggregate into particles, by mixing calcium hydroxide with other hydroxide and water, heating the mixture and pulverizing the resultant aggregate into particles, or by some other method.

However, the soda lime produced as above has an irregular physical form and often has an acute angle partially. For this reason, the soda lime has a problem in that when it is packed in a container, etc., and shipped, its individual particles grind one another by friction to crush the acute angles thereof, which results in formation of a fine powder or dust-like soda lime. That is, this fine powder or dust-like soda lime is inherently corrosive. For example, when there is used a device equipped with a column charged with this soda lime as an absorbent to remove carbon dioxide from a narcotic gas, the fine powder or dust of the soda lime is fed together with the narcotic gas and a narcotized patient might be seriously affected by breathing it in. Further, this soda lime may cause a problem in that its dust flies away into a room and pollutes air in the room when the column is recharged.

There have been proposed a variety of methods to solve these problems. For example, these problems might be solved by coating particle of the soda lime with, e.g. a gelatin-like substance such as dextran, by adding carboxymethyl cellulose to the soda lime (Japanese Patent Publication No. 42-20464), by forming the soda lime into semisperical particles, or by some other method.

Soda lime particles produced according to these methods are not necessarily satisfactory as an absorbent in view of performance and cost. For example, the coating method not only increases the production cost, but also causes a problem in that the capabilitiy of absorbing carbon dioxide is reduced depending upon a gelatin-like substance used to coat the particles. The method using carboxymethyl cellulose is costwise unsatisfactory. Further, although the method of forming semispherical soda lime makes it possible, to some extent, to reduce physical shape-induced formation of a fine powder or duct in transportion, such a semispherical soda lime has a problem in that the formation of a fine powder or dust cannot be satisfactorily prevented due to its low hardness.

SUMMARY OF THE INVENTION

This invention has been made by taking the above situations into consideration, and the present object is to provide a process for the production of an absorbent which is almost free from the formation of a fine powder and dust and which has a high capability of absorbing acidic gas such as carbon dioxide.

The present invention provides a process for producing a molded acidic gas absorbent, which comprises press molding at least one selected from the group consisting of powders, particles and granules of calcium hydroxide and at least one member selected from the group consisting of powders, particles and granules of alkali metal hydroxides and alkaline earth metal hydroxides except for calcium hydroxide, impregnating the resulting molded article with water, and heat treating the resulting article so as to maintain a predetermined amount of water therein.

The present invention also provides a molded acidic gas absorbent comprising calcium hydroxide, and at least one member selected from the group consisting of alkali metal hydroxides and alkaline earth metal hydroxides except for calcium hydroxide, and water, and having an average hardness of 900 to 2600 g and a melt solidified surface in an area of 50% or more.

DESCRIPTION OF THE PREFERRED EMBODIMENTS

Figure 1:
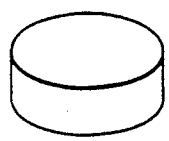
FIGS. 1 to 5 are perspective views of various shapes of the acidic gas absorbent of this invention.

The present inventors have diligently studied a process for the production of an acidic gas absorbent containing soda lime as a main component, in which the formation of a fine powder or dust due to friction and vibration during the transportion is reduced without decreasing the capability of absorbing carbon dioxide in particular. As a result, it was found that an acidic gas absorbent having a high capability of absorbing acidic gas and being almost free from the formation of a fine powder and dust due to friction and vibration during the transportion can be produced by a process which comprises press molding powders, particles and/or granules containing calcium hydroxide and hydroxide of an alkali metal, etc., (the resultant product is abbreviated as "a molded product" hereinbelow), then impregnating the molded product with water and subjecting the molded product to heat treating.

The calcium hydroxide, hydroxide of an alkali metal, etc., and water used in this invention are not particularly limited if they do not contain impurities which cause a problem when the acidic gas absorbent of this invention is used as an absorbent of carbon dioxide contained in air, narcotic gas, etc. Thus, these components are not required to have a specially high purity.

Examples of the hydroxide of an alkali metal used in this invention are hydroxides of alkali metals such as lithium, sodium, potassium, etc. Examples of the hydroxide of an alkaline earth metal other than calcium are barium hydroxide, magnesium hydroxide, etc. These hydroxides of alkali metals, etc., may be used alone or in combination.

The acidic gas absorbent of this invention may be produced as follows.

First, a mixture of a powder, particles and/or granules of calcium hydroxide with a powder, particles and/or granules of hydroxide of an alkali metal, etc., or powders, particles and/or granules of a mixture of calcium hydroxide with hydroxide of an alkali metal, etc., is press molded into a suitable form, e.g. a tablet form (circular plate, disk, etc.). The molded product is then impregnated with water according to an ordinary method such as spraying using a sugar coater, coating pan, or the like. Thereafter, the resultant product is heat treated, whereby an acidic gas absorbent molded product of this invention can be obtained.

The process of this invention has characteristics in this heat treating wherein the molded product is heated so as to maintain a predetermined amount of water therein. It is considered that this treatment brings a state in which at least 50% or more, usually 70% or more, preferably 80% or more, of the resultant acidic gas absorbent molded product surface is melt-solidified to increase the hardness of the absorbent, whereby the formation ratio of a fine powder and dust during the transportion can be consequently reduced.

When the powders, particles and/or granules containing calcium hydroxide and hydroxide of an alkali metal, etc., are press molded, the mixing ratio of the calcium hydroxide and hydroxide of an alkali metal, etc., in the powders, particles and/or granules is preferably adjusted in such a range that the resultant absorbent of this invention can effectively work. Based on 100 parts by weight of the calcium hydroxide, in general, the amount of the hydroxide of an alkali metal, etc., is about 1 to 7 parts by weight, preferably 3 to 5 parts by weight.

The method of press molding is not particularly limited, so long as there is produced a molded product having almost no acute angles which are liable to form a fine powder due to friction, etc. For example, a method using a commercially available tablet-making machine is preferable in view of machine availability and operationability.

The size of the molded product is not particularly limited if the molded product can be filled, in a suitable density, in a column, etc., into which a usual acidic gas absorbent is filled. In general, for example, a tablet of the absorbent has a diameter of 1 to 10 mm, preferably about 2 to 7 mm, and a thickness of 1 to 10 mm, preferably about 1.5 to 3 mm.

The pressure for the press molding is very important. That is, with increasing the pressure, the acidic gas absorption capability of the resultant absorbent decreases, although the formation of a fine powder and dust is reduced. With decreasing the pressure, the formation of a fine powder and dust increases due to low hardness, although the acidic gas absorption capability of the resultant absorbent increases. When the acidic gas absorbent of this invention is produced, the pressure for the molding is usually 200 to 1,300 Kg/cm$^2$, preferably 250 to 800 Kg/cm$^2$, and more preferably 250 to 400 Kg/cm$^2$. The molded product in a circular plate form has an average hardness of 200 to 2,000 g, preferably 300 to 1,200 g, and more preferably about 500 g measured by using a jelly strength measuring apparatus of Japanese Society of Agar Fisheries type.

In general, the molded product is allowed to contain water by fully spraying the water by means of, e.g. a coating pan, and the amount of water contained therein is usually 5 to 21 W/W%, preferably 14 to 19 W/W%.

In the heat treatment of the molded product containing water, the heating temperature is usually 50° to 120° C., preferably 75° to 85° C., and the heating time is usually 1 to 24 hours, preferably 4 to 15 hours. When the heat treating is carried out, it is necessary to take care so as to make the water contained in the molded product hardly evaporate or dissipate. This is because it is an essential requirement of the present acidic gas absorbent to maintain the specified amount of water so as to exhibit the function as the gas absorbent. Therefore, it is preferable to carry out the heat treating in a state that water vapor is nearly saturated. The most simplest method is carried out, for example, by packing the above molded product in a sealable container or bag, bringing it into a sealed or nearly closed state, and carrying out the heat treating in such a state. There is no special limitation to be imposed on methods to be taken actually, if the heat treating can be carried out under such conditions. In addition, the amount of water contained in the acidic gas absorbent of this invention is usually 5 to 21 W/W%, preferably 14 to 19 W/W%.

The acidic gas absorbent of this invention, produced as specified above, has characteristics in that not only the acidic gas absorption capability thereof is high but also the amount of a fine powder and dust formed during the transportation is very small. The acidic gas absorbent of this invention, e.g. in a circular plate-like tablet form, has an average hardness, usually, in the range of from 900 to 2,600 g. Such an absorbent that has a hardness of 900 to 1,400 g in particular is more preferable, since the amount of a formed fine powder and dust is small and the acidic absorption capability thereof is high.

In the acidic gas absorbent of this invention, as can be assumed from its purpose in use, the amounts of individual components contained therein are not required to be constant, and their weights are not required to be constant, either. Nor is it necessary to prepare its appearance, size, etc, uniformly.

An indicator may be incorporated into the acidic gas absorbent of this invention to detect a residual capability of absorbing acidic gas. For example, if an acid-alkali indicator such as ethyl violet, titanium yellow, Congo Red, or the like is incorporated into the acidic gas absorbent of this invention, the absorbent undergoes a color change when the alkalinity of the absorbent decreases by absorbing acidic gas, or in other words, when the acidic gas absorption capability thereof lowers, whereby the time for absorbent replacement can be determined by observing the color change with the eyes. The above acid-alkali indicator can be incorporated into the acidic gas absorbent of this invention by a method of mixing the indicator at a molding time, by a method of dissolving the indicator in water to be contained in the molded product, or by some other method. Any method of these can be used.

Figure 3:
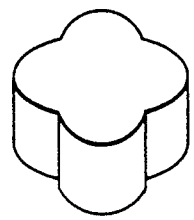
Figure 2:
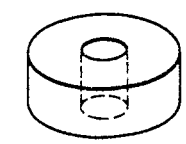
Figure 4:
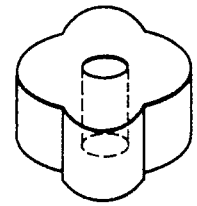
Figure 5:
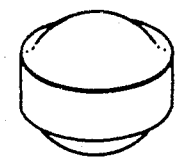

The form of the acidic gas absorbent of this invention is not critical, if it is not a form partically having such an acute angle that is liable to form a fine powder due to friction and attrition. Specific examples of the form are spherical, semispherical, and tablet-type forms. The tablet-type form is, in general, circular plate or disk-like as shown in FIG. 1 and 5. And, forms shown in FIGS. 2 to 4 may be also employed. When the absorbent is formed in one of these forms, the absorbent can have a large surface area, and therefore, it can naturally have improved capability of absorbing acidic gas.

This invention will be explained more in detail by reference to Examples and Comparative Examples, in which all percents are by weight unless otherwise specified.

EXPERIMENTS 1-6

(1) Preparation of tablet-type absorbent of acidic gas

Calcium hydroxide (6 kg) in a powder form and 280 g of sodium hydroxide in a powder form were fully mixed, and then divided into six equal portions. These portions were molded into tablets having a diameter of 5 mm and a height of 2.5 mm by using a commercially available tablet-making machine under a given pressure. The resultant tablets were sprayed and impregnated with water so as to have a water content of 17% by using a commercially available coating pan. Then, the tablets were sealed in a polyethylene bag, and the bag was allowed to stand in a constant temperature oven at 80° C. for 15 hours to give tablet-type absorbents for acidic gas having a melt solidified surface in an area of 80% or more.

In addition, the tablet-type absorbents were measured for a water content (W/W%) to show that the water content was nearly the same as the content of water impregnated by using the coating pan.

(2) Test on carbon dioxide absorption capability

The carbon dioxide absorption capability of the tablet-type absorbents obtained in the above (1) was tested in the following manner.

An oxygen gas containing 4.6% of carbon dioxide was flowed, at a rate of 6,000 ml/min., through a canister (volume 950 ml) charged with 810 g of the tablet-type acidic gas absorbent by using a respirator (Cape Bristol ventilator, supplied by Nippon Medico K.K.), and the time was measured until a trace amount of carbon dioxide leaked in a gas flowing out of the absorbent canister. In addition, the carbon dioxide in the gas was measured by gas chromatography.

The results are shown in Table 1.

(3) Measurement of hardness of tablet-type acidic gas absorbent

The hardness of the tablet-type acidic gas absorbents obtained in the above (1) was measured in the following manner.

Five tablets were selected from each of the tablet-type acidic gas absorbents prepared under predetermined conditions, and the hardness of each of the tablets was measured according to an ordinary method by using a jelly strength measuring apparatus of Japanese Society of Agar Fisheries type (mfd. by Kiya Seisakusho, Ltd.).

The measured values were statistically treated, and shown in Table 1.

(4) Measurement of formation ratio of powder

The formation percentage of a powder formed from the tablet-type acidic gas absorbents obtained in the above (1) due to vibration and friction was measured in the following manner.

The tablet-type acidic gas absorbent (20 g) which was accurately weighed out was put in a glass bottle (volume 250 ml), and the bottle was set in a reciprocating shaker (supplied by Takahashi Seisakusho) and shaken for 7 hours at a shake width of 90 mm and a shake rate of 60 times/min. The resultant substance was sieved to measure a formation percentage (W/W%) of a powder of passing 12 mesh.

Table 1 shows the results.

COMPARATIVE EXAMPLE 1

A commercially available, massive absorbent of carbon dioxide (composed mainly for soda lime) was tested on carbon dioxide absorption capability in the same way as in Experiments 1 to 6. It was also measured for a hardness and powder formation percentage in the same way as Experiments 1 to 6.

Table 1 shows the results.

COMPARATIVE EXAMPLE 2

A commercially available, semipherical absorbent of carbon dioxide (composed mainly of soda lime) was tested for carbon dioxide absorption capability in the same way as in Experiments 1 to 6. It was also measured for a hardness and powder formation rate in the same way as Experiments 1 to 6.

Table 1 shows the results.

TABLE 1

| Experiment Nos. and Comparative Examples | Tablet making pressure ($Kg/cm^2$) | Leakage point (hr) | Tablet hardness (n = 5) (g) | Powder formation percentage (%) |
| --- | --- | --- | --- | --- |
| Experiment 1 | 150 | 6 | 600 | 1.2 |
| Experiment 2 | 300 | 6 | 1150 | 0.3 ↓ |
| Experiment 3 | 700 | 5 | 1150 | 0.3 ↓ |
| Experiment 4 | 1200 | 4 | 1150 | 0.3 ↓ |
| Experiment 5 | 1600 | 3 | 2100 | 0.3 ↓ |
| Experiment 6 | 2800 | 1 | 3000 | 0.3 ↓ |
| Comparative Example 1 | — | 4 | 1000 | 1.5 |
| Comparative Example 2 | — | 5.5 | 300 | 0.8 |

Table 1 clearly shows that the tablet-type acidic gas absorbents produced according to the process of this invention at a tablet-making pressure of 300 to 1,200 $Kg/cm^2$ exhibit a clearly lower power formation percentage than commercially available, carbon dioxide absorbents, and have a carbon dioxide absorption capability equivalent to or higher than those of the commercially available, carbon dioxide absorbents.

EXAMPLES 1–3

(1) Preparation of tablet-type acidic gas absorbent

Calcium hydroxide (3 kg) in a powder form and 140 g of sodium hydroxide in a powder form were fully mixed, and the mixture was molded into tablets having a diameter of 5 mm and a height of 2.5 mm by using a commercially available tablet-making machine at a tablet-making pressure of 300 kg/cm$^2$ (the resultant tablets had an average hardness of 500 g). The molded tablets were separated into three equal groups, and each group of the tablets was sprayed and impregnated with water so as to contain a predetermined amount of water by using a commercially available coating pan. Then, the tablets were sealed into a polyethylene bag, and the bag was allowed to stand in a constant temperature oven at 80° C. for 15 hours to give tablet-type acidic gas absorbents having a melt solidified surface in an area of 80% or more.

The tablet-type acidic gas absorbents were measured for a water content (W/W%) to show that the water content was nearly the same as that of water impregnated by using the coating pan.

(2) Performance test

The tablet-type acidic gas absorbents obtained in the above (1) were tested on carbon dioxide absorption capability in the same way as in Experiments 1 to 6, and measured for an average hardness and a powder formation ratio in the same way as in Experiments 1 to 6.

Table 2 shows the results. For comparison, Table 2 also shows the results of comparative Examples 1 and 2.

TABLE 2

| Example No. | Water content W/W % | Leakage point (hr) | Tablet hardness (n = 5) (g) | Powder formation percentage (%) |
| --- | --- | --- | --- | --- |
| Example 1 | 10 | 5 | 1150 | 0.3 ↓ |
| Example 2 | 15 | 5 | 1150 | 0.3 ↓ |
| Example 3 | 18 | 5 | 1150 | 0.3 ↓ |
| Comparative Example 1 | — | 4 | 1000 | 1.5 |
| Comparative Example 2 | — | 5.5 | 300 | 0.8 |

Table 2 clearly shows that the tablet-type acidic gas absorbents of this invention obtained in Examples 1 to 3 exhibit a clearly lower powder formation percentage than those of the commercially available carbon dioxide absorbents, and have carbon dioxide absorption capability equivalent to or higher than those of the commercially available carbon dioxide absorbents.

EXAMPLES 4–5

(1) Preparation of tablet-type acidic gas absorbent

Calcium hydroxide (3 kg) in a powder form and 140 g of sodium hydroxide in a powder form were fully mixed and the mixture was molded into tablets having a diameter of 5 mm and a height of 2.5 mm by using a commercially available tablet-making machine at a tablet-making pressure of 300 kg/cm$^2$ (the resultant tablets had an average hardness of 500 g). The molded tablets were sprayed and impregnated with water so as to have a water content of 17% by using a commercially available coating pan. Then, the tablets were separated into two equal portions in number and sealed into a polyethylene bag, and the bag was allowed to stand in a constant temperature oven at 80° C. for a given period of time to give tablet-type acidic gas absorbents having a melt solidifed surface in an area of 80% or more.

The tablet-type acidic gas absorbents were measured for a water content (W/W%) to show that the water content was nearly the same as that of water impregnated by using the coating pan.

(2) Performance test

The tablet-type acidic gas absorbents obtained in the above (1) were tested on carbon dioxide absorption capability in the same way as in Experiments 1 to 6, and measured for an average hardness and a powder formation percentage in the same way as in Experiments 1 to 6.

Table 3 shows the results.

COMPARATIVE EXAMPLE 3

Calcium hydroxide (3 kg) in a powder form and 140 g of sodium hydroxide in a powder form were fully mixed, and the mixture was then molded into tablets having a diameter of 5 mm and a height of 2.5 mm by using a commercially available tablet-making machine at a tablet-making pressure of 300 kg/cm$^2$ (the resultant tablets had an average hardness of 500 g). The molded tablets were sprayed and impregnated with water so as to have a water content of 17% by using a commercially available coating pan to give tablet-type absorbents.

These tablet-type absorbents were tested on carbon dioxide absorption capability in the same way as in Experiments 1 to 6, and measured for an average hardness and a powder formation ratio in the same way as in Experiments 1 to 6.

Table 3 shows the results. For comparison, Table 3 also shows the results of Comparative Examples 1 and 2.

TABLE 3

| Example No. | Heat treating time (hr) | Leakage point (hr) | Tablet hardness (n = 5) (g) | Powder formation percentage (%) |
| --- | --- | --- | --- | --- |
| Example 4 | 4 | 6 | 1000 | 0.3 ↓ |
| Example 5 | 15 | 6 | 1150 | 0.3 ↓ |
| Comparative Example 3 | 0 | 5 | 560 | 1.2 |
| Comparative Example 1 | — | 4 | 1000 | 1.5 |
| Comparative Example 2 | — | 5.5 | 300 | 0.8 |

Table 3 clearly shows that the tablet-type acidic gas absorbents of this invention obtained in Examples 4 and 5 exhibit a clearly low powder formation percentage than those of the commercially available carbon dioxide absorbents, and have carbon dioxide absorption capability equivalent to or higher than those of the commercially available carbon dioxide absorbents.

Further, Table 3 also shows that the absorbent obtained in Comparative Example 3, which was treated so as to contain water but was not heat treated, had a powder formation percentage nearly equivalent to those of the commercially available carbon dioxide absorbents, although it had a higher carbon dioxide absorption capability than the commercially available carbon dioxide absorbents.

As described above, the acidic gas absorbent of this invention has characteristics in that it has not only a higher capability of absorbing acidic gas but also a lower fine powder formation ratio than conventional acidic gas absorbents. Therefore, the acidic gas absorbent of this invention is industrially very useful since it makes it possible to overcome the problems of conventional absorbents caused by a fine powder of soda lime, e.g. air pollution in a room caused at a time of recharging the absorbent, risk that a narcotized patient might breathe in a soda lime fine powder when the absorbent is used to remove carbon dioxide from a narcotic gas, and the like.

What is claimed is:

1. A process for producing a molded acidic gas absorbent, which comprises press molding at least one member selected from the group consisting of powders, particles and granules of calcium hydroxide and at least one member selected from the group consisting of powders, particles and granules of alkali metal hydroxides and alkaline earth metal hydroxides except for calcium hydroxide, in an amount of about 1 to about 7 parts by weight per 100 parts by weight of said calcium hydroxide, to form a molded article;

impregnating said molded article with water, and heat treating the resulting article at about 50° to 120° C. for about 1 to 24 hours in a substantially closed system, so as to maintain about 5 to about 21 W/W% water therein and to produce a molded adsorbent having a melt solidified surface of at least about 50%.

2. A process according to claim 1, wherein the press molding is carried out under a pressure of 200 to 1,300 kg/cm².

3. A process according to claim 1, wherein said molded article is at least one tablet.

4. A process claimed in claim 1 consisting essentially of the recited steps.

5. A molded acidic gas absorbent comprising calcium hydroxide; at least one member selected from the group consisting of alkali metal hydroxides and alkaline earth metal hydroxides, except for calcium hydroxide; and water, and having an average hardness of 900 to 2600 g and a surface which has a melt solidified area of at least 50% prepared by the process of claim 1.

6. A molded acidic gas absorbent comprising calcium hydroxide, at least one alkali metal hydroxide, and water, and having an average hardness of 900 to 2600 g and a surface which has a melt solidified area of at least 50% prepared by the process of claim 1.

7. A molded acidic gas absorbent according to claim 6, wherein the alkali metal hydroxide is sodium hydroxide.

* * * * *